(12) United States Patent
Lai et al.

(10) Patent No.: US 7,371,557 B2
(45) Date of Patent: May 13, 2008

(54) SACCHAROMYCES CEREVISIAE STRAINS FOR HYPER-PRODUCING GLUTATHIONE AND γ-GLUTAMYLCYSTEINE AND PROCESSES OF USE

(75) Inventors: Jinn-Tsyy Lai, Hsinchu (TW); Shin-Ying Lee, Hsinchu (TW); Chun-Chieh Hsieh, Pingtung (TW); Chin-Fa Hwang, Hsinchu (TW); Chii-Cherng Liao, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 0 days.

(21) Appl. No.: 11/359,722

(22) Filed: Feb. 22, 2006

(65) Prior Publication Data

US 2007/0196382 A1 Aug. 23, 2007

(51) Int. Cl.
*C12N 1/20* (2006.01)
*C12P 21/06* (2006.01)

(52) U.S. Cl. .................................. 435/252.3; 435/69.1

(58) Field of Classification Search ............. 435/252.3, 435/69.1
See application file for complete search history.

(56) References Cited

U.S. PATENT DOCUMENTS 4,582,801 A 4/1986 Hamada et al.
2005/0239164 A1* 10/2005 Perrone et al. ............. 435/69.1

FOREIGN PATENT DOCUMENTS

EP 1 201 747 5/2002

OTHER PUBLICATIONS

Tateishi, N. et al. "Studies on the Regulation of Glutathione Level in Rat Liver" *J. Biochem.* (1974) vol. 75, No. 1, pp. 93-103.

Issels, R. D. et al. "Promotion of Cystine Uptake and Its Utilization for Glutathione Biosynthesis Induced by Cysteamine and N-Acetylcysteine" *Biochemical Pharmacology* (1988) vol. 37, No. 5, pp. 881-888.
Meister, A. et al. "Glutathione" *Ann. Rev. Biochem.* (1983) vol. 52, pp. 711-760.
Schofield, J.D. et al. "Analysis of Free Reduced and Free Oxidised Glutathione in Wheat Flour" *Journal of Cereal Science* (1995) vol. 21, pp. 127-136.
Alfafara, C. et al. "Cysteine Addition Strategy for Maximum Glutathione Production in Fed-Batch Culture of *Saccharomyces cerevisiae*" *Applied Microbiology and Biotechnology* (1992) vol. 37, pp. 141-146.
Shimizu, H. et al. "Optimal Production of Glutathione by Controlling the Specific Growth Rate of Yeast in Fed-Batch Culture" *Biotechnology and Bioengineering* (1991) vol. 38, pp. 196-205.
English Abstract of EP 0300168 dated Jan. 25, 1989.
English Abstract of JP 61074596 dated Apr. 16, 1986.
English Abstract of EP 1 201 747 dated May 2, 2002.
English Abstract of TW 222235 dated Mar. 30, 1992.
English Abstract of JP 60248199 dated Dec. 7, 1985.
English Abstract of JP 60024197 dated Feb. 6, 1985.
English Abstract of JP 59034899 dated Feb. 25, 1984.
English Abstract of JP 58016694 dated Jan. 31, 1983.
English Abstract of JP 56082099 dated Jul. 4, 1981.
English Abstract of JP 52156994 dated Dec. 27, 1977.
English Abstract of JP 1141591 dated Jun. 2, 1989.
English Abstract of JP 62283994 dated Dec. 9, 1987.

* cited by examiner

*Primary Examiner*—Mark Navarro
(74) *Attorney, Agent, or Firm*—Ladas & Parry LLP

(57) ABSTRACT

The present invention provides a biologically pure culture of *Saccharomyces cerevisiae* strain YA02032 or YA03083, which culture has a characteristic nature capable of producing glutathione and the precursor thereof, γ-glutamylcysteine. A composition comprising the culture and a process for the production of glutathione and/or the precursor thereof, γ-glutamylcysteine, are also provided.

29 Claims, 9 Drawing Sheets

SACCHAROMYCES CEREVISIAE STRAINS FOR HYPER-PRODUCING GLUTATHIONE AND γ-GLUTAMYLCYSTEINE AND PROCESSES OF USE

BACKGROUND OF THE INVENTION

1. Field of the Invention

The invention relates to *Saccharomyces cerevisiae* strains and processes for hyper-producing glutathione and γ-glutamylcysteine.

2. Description of the Related Art

Glutathione (GSH), a small peptide composed of L-glutamic acid, L-cysteine and glycine, is a natural antioxidant. It was first isolated in 1888 and formally named in 1921. Glutathione is broadly found in organisms including animals, plants and microorganisms. Its metabolism and physiological functions in animal cells, and processes for hyper-producing it are well documented (Tateishi N. et. al., 1974. J B. 75: 93-103; Issels R. et al., 1988. *Biochem Pharmacol.* 37: 881-888; and Meister, A. et al., 1983. *Ann. Rev. Biochem.* 52: 711-60). Glutathione has been used in liver protectors, scavengers of toxins and eye drops. It is also a promising ingredient of functional health food products.

The industrial processes for producing glutathione includes chemical synthesis, extraction, enzymatic production, and fermentation, among which fermentation is preferred because of its easy manipulation. Furthermore, glutathione produced by fermentation using yeasts is safer to be used in food products than the same compound produced by fermentation methods using other microorganisms, such as recombinant *Escherichia coli*. As a reason, yeast is widely utilized for preparing the glutathione for use in functional drinks and health food products. Yeast mutants produced by mutagens such as amide and indophenols, which improve glutathione production, have been also reported (JP60248199).

The product γ-glutamylcysteine (γ-GC) is a precursor of glutathione in the synthesis process. It is reported that γ-glutamylcysteine is effective in lowering the damage of $CCl_4$ to the liver in a mouse. The product has functions similar to glutathione, and can regulate the glutathione content in a cell when co-exists with glutathione synthetase. In addition, γ-glutamylcysteine is an important content of human milk and can enhance immunogenesis ability of a subject.

SUMMARY OF THE INVENTION

One object of the invention is to provide a biologically pure culture of a microorganism strain comprising all characteristics of the *Saccharomyces cerevisiae* strain selected from the group consisting of YA02032 and YA03083. Said culture has the characteristic nature capable of producing glutathione and the precursor thereof, γ-glutamylcysteine.

Another object of the invention is to provide a composition comprising the culture according to the invention.

Yet another object of the invention is to provide a process for the production of glutathione and/or the precursor thereof, γ-glutamylcysteine, which is characterized by cultivating the biologically pure culture of the invention.

BRIEF DESCRIPTION OF THE DRAWINGS

FIG. 4 Influence of single amino acid addition on glutathione and γ-glutamylcysteine production.

FIG. 5 Influence of different amino acids addition on glutathione and γ-glutamylcysteine production.

DETAILED DESCRIPTION OF THE INVENTION

Figure 1:
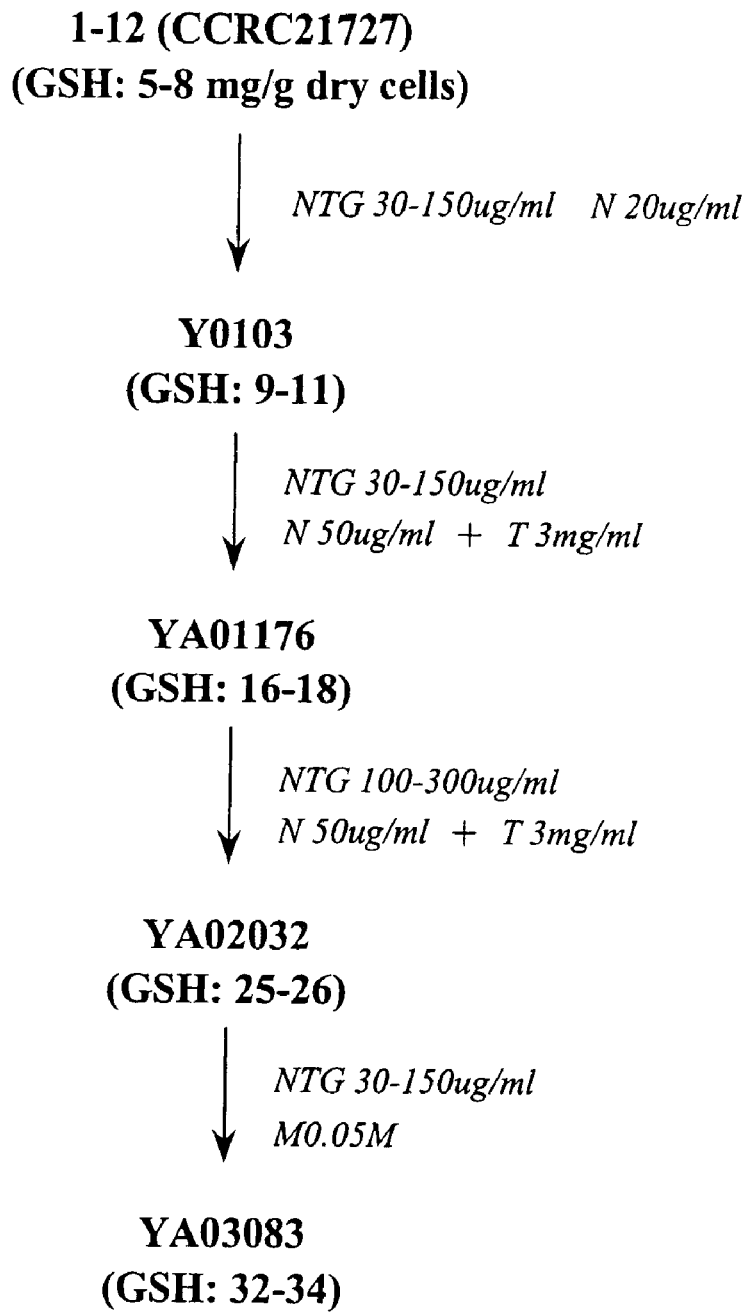
FIG. 1 Genealogy of glutathione hyper-producing strains from wild type *Saccharomyces cerevisiae* 1-12 (CCRC21727). N: sodium azide. T: 1,2,4-triazole. M: methylglyoxal. B: benzyl chloride.

Yeast is capable of producing glutathione. The invention provides novel and stable *Saccharomyces cerevisiae* strains capable of hyper-producing glutathione and the precursor thereof, γ-glutamylcysteine. A process for producing glutathione and/or the precursor thereof is also illustrated in the present invention.

The invention provides a biologically pure culture of a microorganism strain comprising all characteristics of the *Saccharomyces cerevisiae* strain selected from the group consisting of YA02032 and YA03083, which culture has a characteristic nature capable of producing glutathione and the precursor thereof, γ-glutamylcysteine.

YA02032 and YA03083 are both derived from *Saccharomyces cerevisiae* 1-12 deposited at the Food Industry Research and Development Institute (FIRDI), Hsinchu, Taiwan, R.O.C. under accession number CCRC21727. The strain *Saccharomyces cerevisiae* 1-12 (CCRC21727) produces 5 to 8 mg/g dry cells of glutathione in the assay according to the invention. The *Saccharomyces cerevisiae* 1-12 (CCRC21727) strain is subjected to mutagenesis with 30 to 300 μg/mL of N-methyl-N'-nitro-N-nitrosoguanidine (NTG) for 15 to 20 min. and the mutated strains obtained are screened with a screen medium containing oxidants and/or toxins, such as sodium azide ($NaN_3$), 1,2,4-triazole and methylglyoxal. When culturing the mutated strains with a screen medium with elevated concentrations of oxidants, the strains having ability to hyper-produce glutathione and/or the precursor thereof can be screened from generation to generation. According to the invention, YA02032 strain is obtained after three-generations of mutagenesis and screening, which stably produces 25 to 26 mg/g dry cell weight of glutathione. YA03083 is further obtained by mutating YA02032 and screening the mutated strains, which stably produces 32 to 34 mg/g dry cell weight of glutathione. The yield of glutathione by YA03083 is four-fold higher than that of the wild type strain, *Saccharomyces cerevisiae* 1-12 (CCRC21727).

The strains according to the invention are very stable and retain the ability to produce glutathione and the precursor thereof with high yield even after several passages and storage for a long time. In the assay of the invention, YA02032 and YA03083 retain genetic stability and produce glutathione and the precursor thereof with high yield even after thirty generations. In addition, YA02032 and YA03083 are also active in hyper-producing glutathione and the precursor thereof even after three-years' storage. As such, the strains according to the invention are qualified for use in industrial fermentation.

The morphological characteristics of YA02032 and YA03083 are similar to those of the wild type strain *Saccharomyces cerevisiae* 1-12 (CCRC21727). The media commonly used for culturing yeasts are suitable for culturing YA02032 and YA03083. In one embodiment of the invention, the medium for culturing the strains of the invention is a YA medium (pH5.1) containing 3 g/L yeast extract, 3 g/L malt extract, 5 g/L peptone, and 10 g/L dextrose. In one embodiment of the invention, YA02032 and YA03083 are cultured at 20 to 40° C. under aerobic conditions.

The present invention also provides a composition comprising the culture of the invention.

*Saccharomyces cerevisiae* has been consumed by human being for thousands of years and is regarded as a microorganism safe for human consumption. The composition of the invention comprises the biologically pure culture of the microorganism strain according to the invention. Preferably, the composition according to the invention is a pharmaceutical composition or a food composition. In one preferred embodiment of the invention, the composition is a functional drink or a health food product.

The present invention further provides a process for the production of glutathione and the precursor thereof, γ-glutamylcysteine, which is characterized by cultivating the biologically pure culture of a microorganism of the invention in a suitable medium.

Preferably, the culture medium comprises an amino acid. Glutathione is composed of L-glutamic acid, L-cysteine and glycine. Therefore, adding an amino acid into the culture medium benefits the productions of glutathione and the precursor thereof. Preferably, the amino acid is one selected from the group consisting of cysteine, glycine and glutamic acid. Most preferably, the amino acid is cysteine. Adding glycine or cysteine benefits the production of γ-glutamylcysteine. In addition, adding cysteine also benefits the production of glutathione. Combining cysteine and glycine benefits the production of glutathione, and almost all the γ-glutamylcysteine is converted to glutathione. Combining cysteine and glutamic acid benefits the production of both glutathione and γ-glutamylcysteine. Preferably, the amino acid has a concentration in a range of 0.1% to 0.75%.

The timing the amino acid is added influences the yields to different degrees. Preferably, the amino acid is added to the culture medium at 15 to 48 hours from the commencement of fermentation.

The fermentation can be performed in a manner well known to persons of ordinary skill of the art. Preferably, the cultivation is a batch cultivation or fed-batch cultivation. More preferably, the cultivation is a fed-batch cultivation. The glutathione yield and dry cell weight in the batch cultivation are both satisfactory. Furthermore, the glutathione yield and dry cell weight obtained in the fed-batch cultivation are better than those obtained in the batch cultivation.

The temperature of the process according to the invention is similar to that of a common fermentation using yeast. Preferably, the microorganism is cultivated at a temperature in a range of 20 to 40° C. More preferably, the microorganism is cultivated at a temperature of 30° C.

The pH value of the cultivation according to the invention is acidic to neutral. Preferably, the microorganism is cultivated at a pH value in a range of 3 to 7. More preferably, the microorganism is cultivated at a pH value of 7.

The glutathione and γ-glutamylcysteine exist in the microorganisms or in the culture medium. The process according to the invention further comprises a step of recovering the glutathione and/or γ-glutamylcysteine from the liquid culture medium. The recovery can be performed in a manner well known to persons of ordinary skill of the art.

The following Examples are given for the purpose of illustration only and are not intended to limit the scope of the present invention.

Strain: The strain used in the example is *Saccharomyces cerevisiae* 1-12 (CCRC21727) and the mutants thereof.

Shake flask culture: Glycerol-stored CCRC21727 was plated on an agar plate and cultivated at 30° C. for two days. A fresh single colony was then inoculated into a 4.75 mL of YM medium (3 g/L yeast extract, 3 g/L malt extract, 5 g/L peptone, 10 g/L dextrose, pH 5.1) and cultured at 30° C. with a stirring speed of 150 rpm for 24 hours. Five percent of the cultivation was further inoculated into a screen medium (60 g/L glucose, 30 g/L peptone, 30 g/L yeast extract, pH 5.1) and cultured for 24 to 48 hours under the same condition.

Fermentor culture: A fresh single colony was inoculated into a 50 mL of YM medium. After 24-hour cultivation, 3 to 5% of the culture was inoculated into a 100 mL of active medium (60 g/L glucose, 12 g/L peptone, 12 g/L yeast extract, 1 g/L $MgSO_4·7H_2O$, pH 5.1) under the same condition. Five percent of the cultivation was further inoculated into a 5 L fermentor containing a main medium (55 g/L glucose, 8.3 g/L molasses sugar, 7 g/L corn steep liquid, 4 g/L $(NH_4)_2SO_4$, 6 g/L $KH_2PO_4$, 2.9 g/L $(NH_4)H_2PO_4$, 1.5 g/L $MgSO_4·7H_2O$, pH 5.1). The common condition of fermentation was with a temperature of 30° C., a stirring speed of 500 rpm and an aeration of 1 L/min.

Mutagenesis: The cultivation fresh cultured at 30° C. for 3 hours was washed with a sterile phosphate buffer twice and then added with 30 to 300 μg/mL NTG. The cells and NTG were mixed and stayed for 15 min. The cells after two-time wash with a phosphate buffer were plated onto a screen plate containing 1,2,4-triazole, $NaN_3$, benzyl chloride, and methylglyoxal. The plate was cultured at 30° C. for 3 to 7 days for screening the mutated strains.

Color reaction for estimating glutathione: One-mL of culture was centrifuged for collecting cell pellets. The pellets were added with the same volume of 0.1 N acetic acid for acid extraction. The extracted cells were boiled in water for 10 min and stayed on ice. A further centrifugation was carried out for obtaining the supernatant. The supernatant was added with 3 mL of a reaction solution (0.6 mM 5,5'-dithiobis-2-nitrobenzoic acid, DTNB, 0.1 M phosphate buffer, pH 7) and mixed well. After reacting for 10 min, the $OD_{412}$ absorbance of the solution was assayed for estimating the sulfur contents thereof.

High performance liquid chromatography (HPLC) for analyzing glutathione and γ-glutamylcysteine: The acid-extract solution as mentioned above was subjected to an HPLC assay. 0.5 mL of the supernatant was added with 0.1 mL of 40 mM iodoacetic acid and 0.2 mL of 1M $NaHCO_3$. The mixture was reacted in dark for 1 hour and then added with a color agent of 0.5 mL of 1.5% 1-fluoro-2,4-dinitrobenzene, FDNB for an overnight reaction. The reaction solution was then centrifuged at 12,000 rpm for 5 min and filtrated. The condition of HPLC was listed below (Schofield, J. D., and X. Chen. 1995. *J. Cereal Science.* 21: 127-136):

mobile phase: buffer A: 80% methanol; buffer B: 200 mL of sodium acetate solution (272 g of sodium acetate trihydrate in 122 mL of water and 378 mL of glacial acetic acid) and 800 mL of buffer A chromatography column: Lichrosorb™ NH$_2$ column flow rate: 1 mL/min detector: UV detector at 365 nm

EXAMPLE 1

Strain Mutagenesis and Screen

*Saccharomyces cerevisiae* 1-12 (CCRC21727) was subjected to NTG mutagenesis and the mutants were screened by the oxidants and/or toxins of 1,2,4-triazole, NaN$_3$, benzyl chloride, and methylglyoxal. The more amounts of NTG and oxidants and/or toxins were utilized, the higher yield of glutathione was obtained. The glutathione yield of the wild-type strain of *Saccharomyces cerevisiae* 1-12 (CCRC21727) was 5 to 8 mg/g dry cells. After four-generations of mutagenesis and screening, YA02032 having a glutathione yield of 25 to 26 mg/g dry cells and YA03083 having a glutathione yield of 34 mg/g dry cells were obtained from about 8,000 mutants. As can be seen, the glutathione yields of the strains of the invention were about four-fold higher. The process and genealogy were shown in FIG. 1.

YA02032 and YA03083 were deposited at the Deutsche Sammlung von Mikroorganismen und Zellkulturen GmbH (DSMZ), Mascheroder Weg 1b, D38124, Braunschweig, Germany under accession numbers DSM 17789 and DSM 17790, respectively.

EXAMPLE 2

Stability

The wild-type strain *Saccharomyces cerevisiae* 1-12 (CCRC21727), and YA02032 and YA01176 were continuously passed for 30 generations and the yields thereof were estimated.

Figure 2:
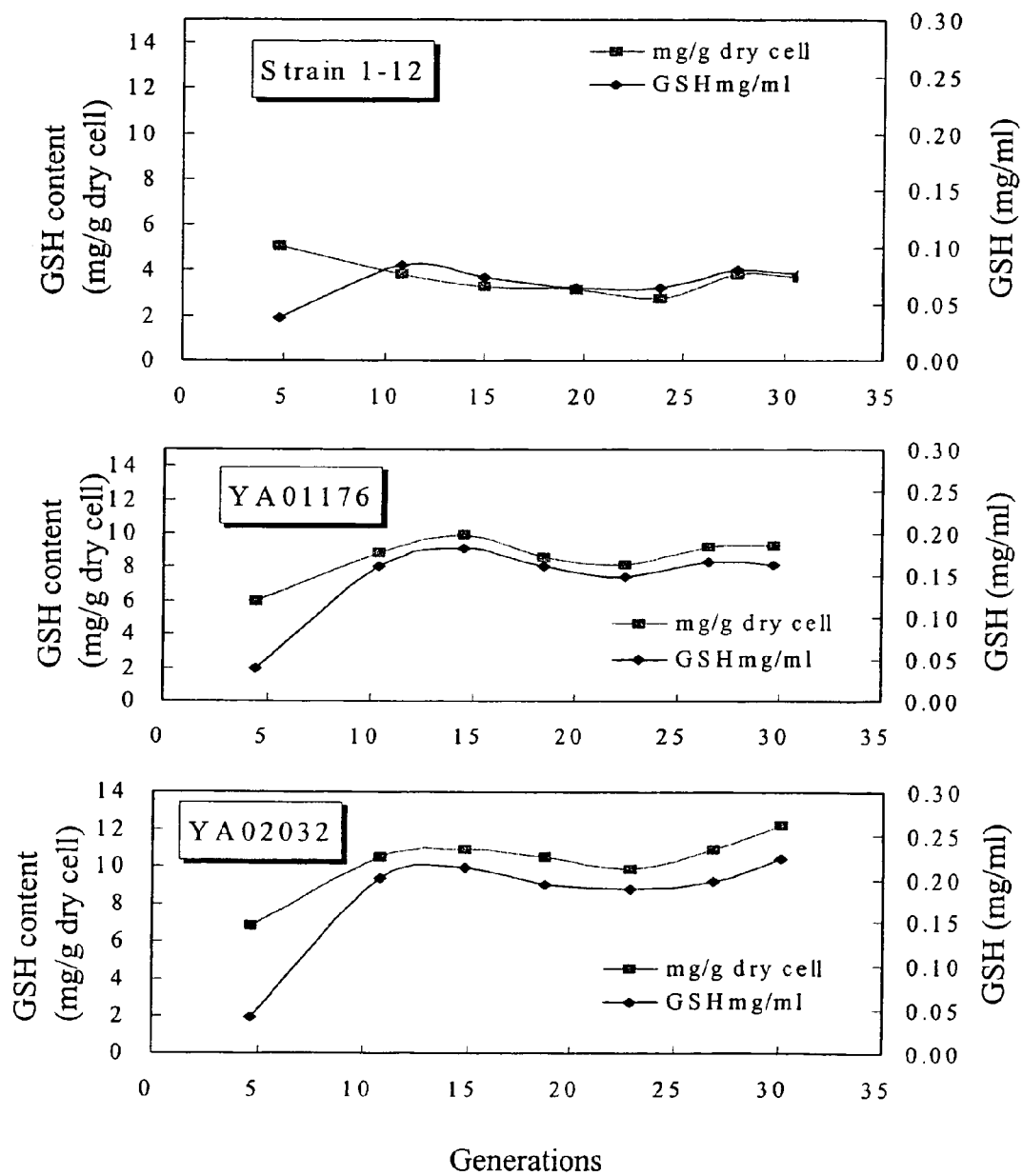
FIG. 2 Results of stability tests for glutathione producing mutants under different generations.

The results are shown in FIG. 2. As shown, the strains of the invention have a good stability.

Separately, the wild-type strain *Saccharomyces cerevisiae* 1-12 (CCRC21727), and YA02032 and YA03083 were subjected to a long-term storage assay. The results are illustrated in Table. 1. The glutathione yield, dry cell weight and survival rate of the lyophilized cells stored at 4° C. for 3 years were similar to fresh cells without significant changes. As such, the storage stability was satisfactory.

TABLE 1

| Strain | Cells (cfu/mL) | dry cell weight (g/L) | GSH (mg/mL) |
|---|---|---|---|
| 1–12 | 4.0 × 10$^8$ | 8.31 | 0.0708 |
| YA02032 | 1.4 × 10$^9$ | 7.68 | 0.1122 |
| YA03083 | 4.4 × 10$^9$ | 8.66 | 0.1609 |

EXAMPLE 3

Medium Modification

Figure 3:
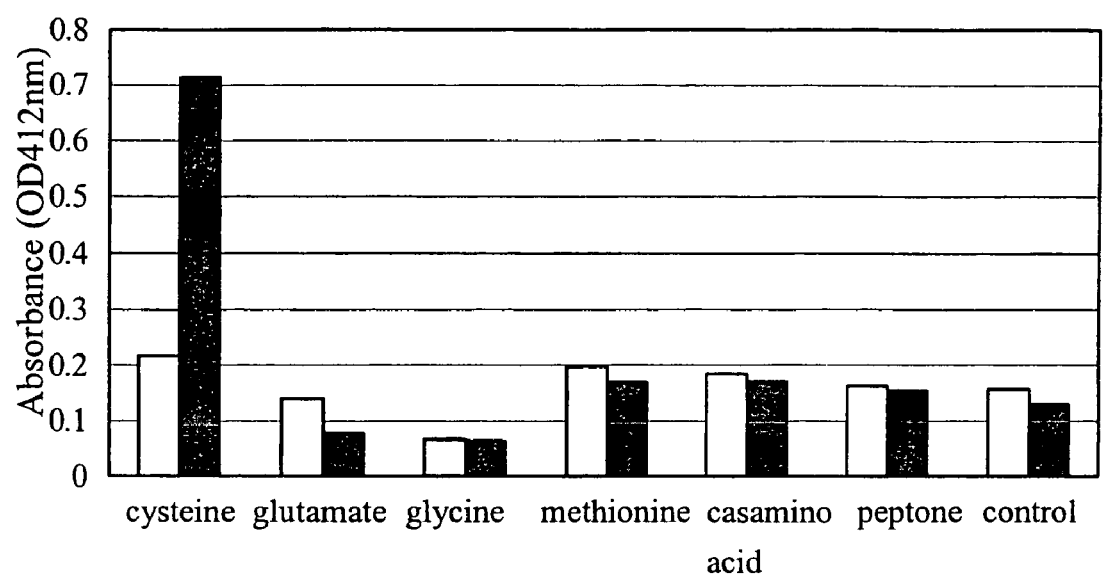
FIG. 3 Comparison of different amino-acids addition on intracellular sulfur-containing compounds by YA02032. Hollow bar: adding at the beginning. Solid bar: adding on hour 15.
Figure 4A:
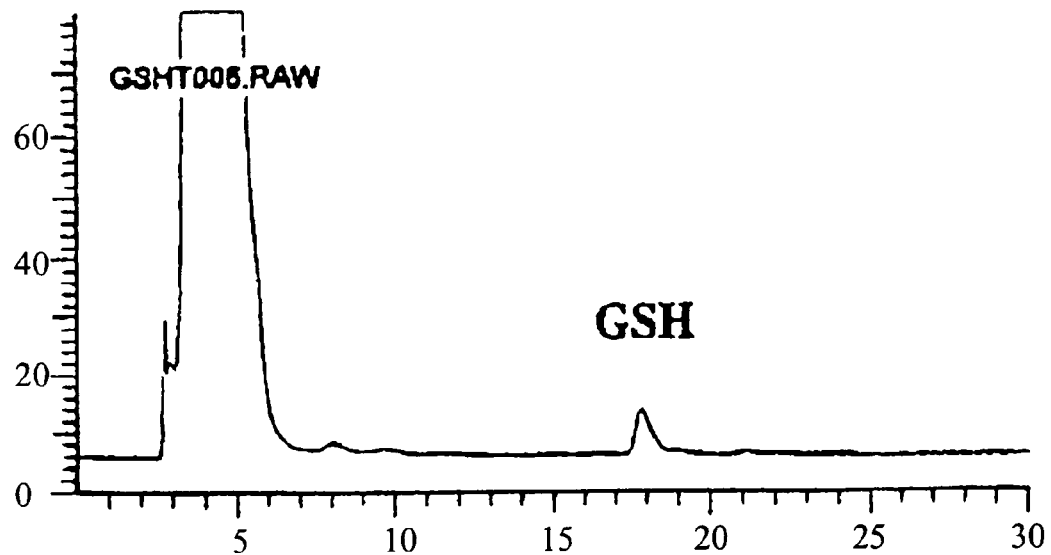
FIG. 4*a*: without amino acid addition.
Figure 4B:
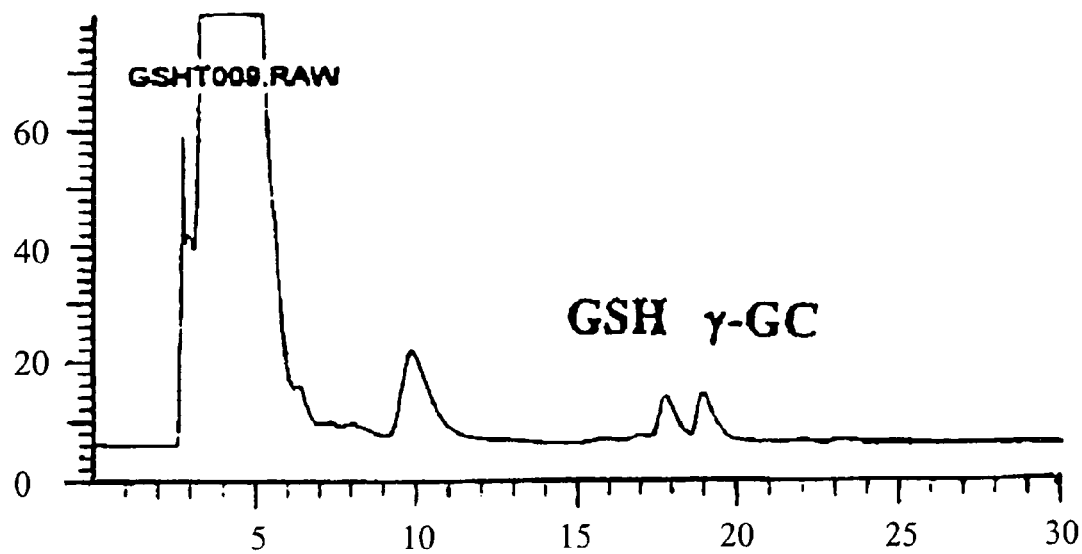
FIG. 4*b*: adding 0.2% cysteine.
Figure 4C:
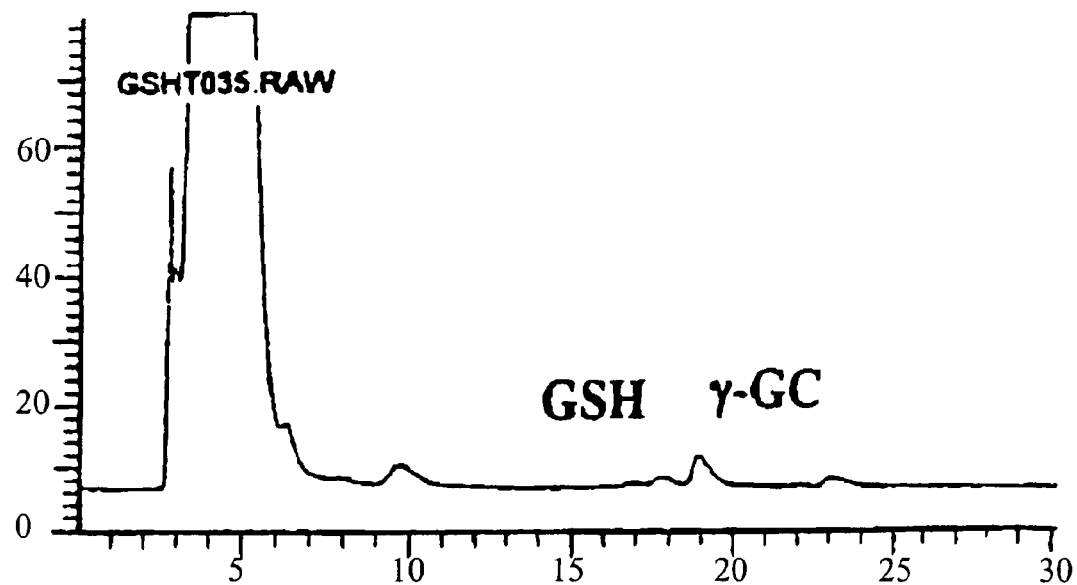
FIG. 4*c*: adding 0.2% glycine.
Figure 4D:
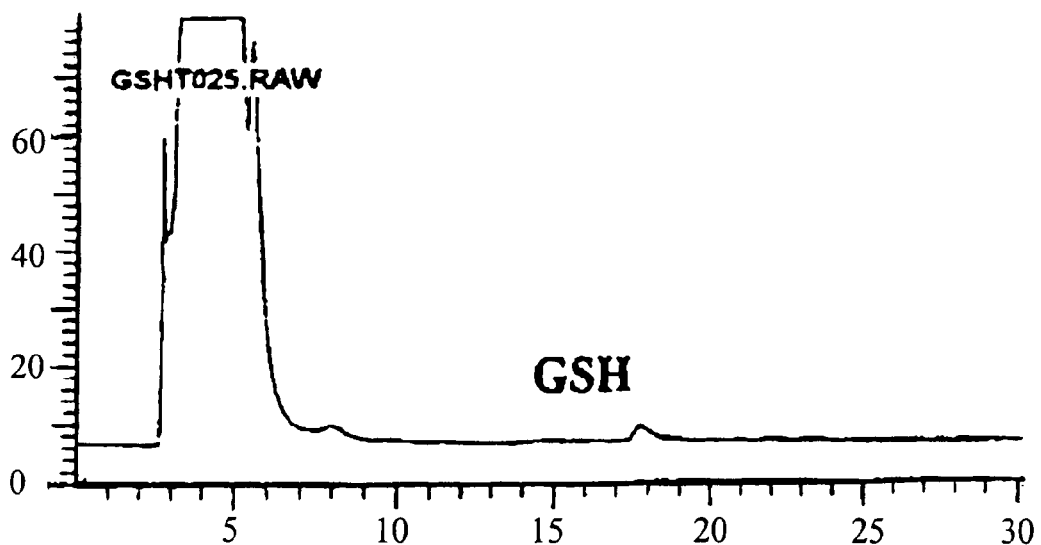
FIG. 4*d*: adding 0.2% glutamic acid.
Figure 5A:
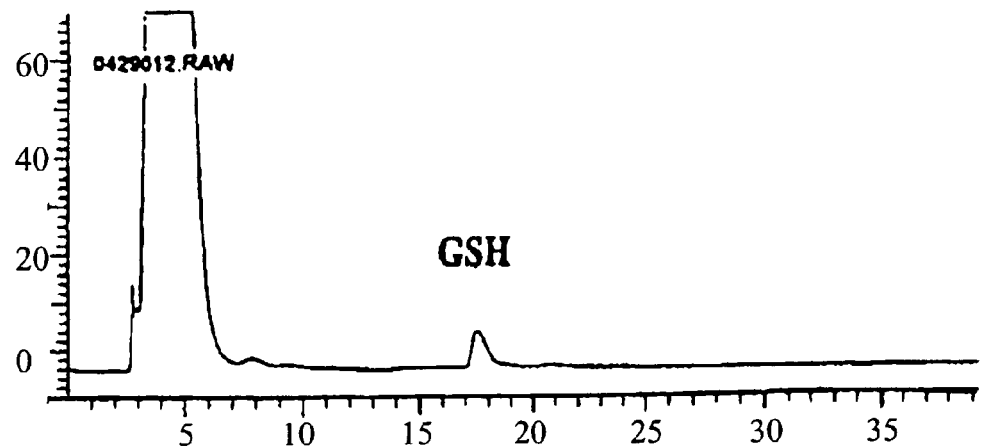
FIG. 5*a*: without amino acid addition.
Figure 5B:
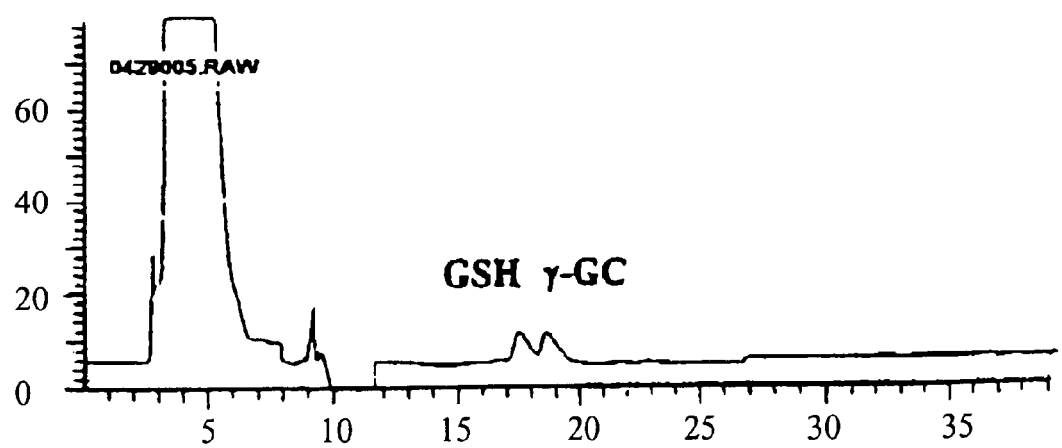
FIG. 5*b*: adding 0.2% cysteine.
Figure 5C:
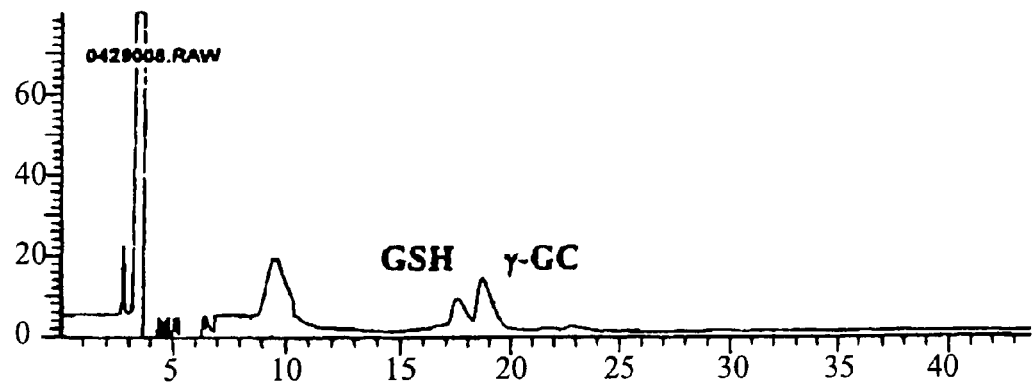
FIG. 5*c*: adding 0.2% cysteine and 0.2% glutamic acid.
Figure 5D:
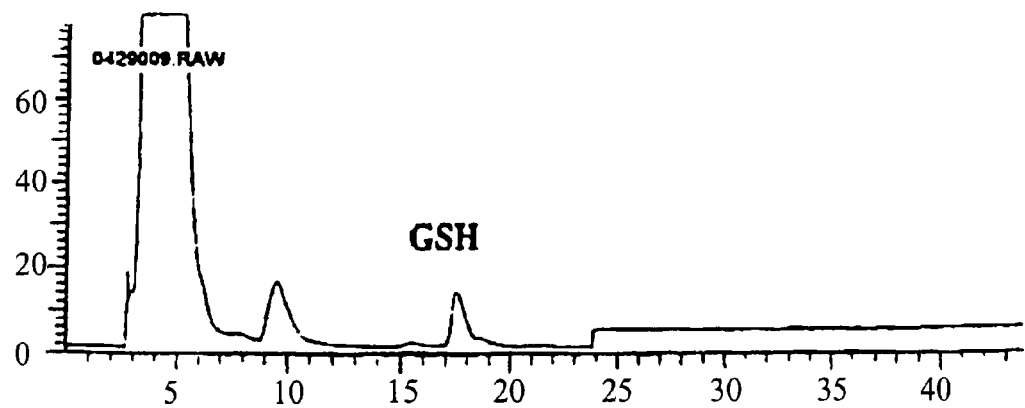
FIG. 5*d*: adding 0.2% cysteine and 0.1% glycine.

For improving glutathione production, L-cysteine, glycine, methionine, glutamic acid, casamino acid, and peptone were added into the culture medium at the beginning of fermentation or at hour 15 of the YA02032 cultivation. The results of absorbance at 412 nm are shown in FIG. 3. It shows that the intracellular sulfur contents were a little improved when adding the amino acids at beginning. However, the sulfur contents were raised enormously. It should be noted that adding cysteine has the best effect.

HPLC was further utilized for analyzing the distribution of glutathione and γ-glutamylcysteine. The results are shown in FIG. 4. It was found that adding glycine inhibits glutathione production and adding cysteine leads to the accumulation of γ-glutamylcysteine without glutathione increasing. Solely adding glutamic acid induces neither γ-glutamylcysteine nor glutathione production.

Because cysteine improves the accumulation of γ-glutamylcysteine, combining cysteine and other amino acids was also assayed and the results are illustrated in FIG. 5. As can be seen, combining cysteine and glycine benefits the glutathione production, and almost all γ-glutamylcysteine is converted to glutathione. Combining cysteine and glutamic acid benefits both the glutathione and γ-glutamylcysteine productions.

EXAMPLE 4

Cultivation in a Five-Liter Fermentor

Figure 6:
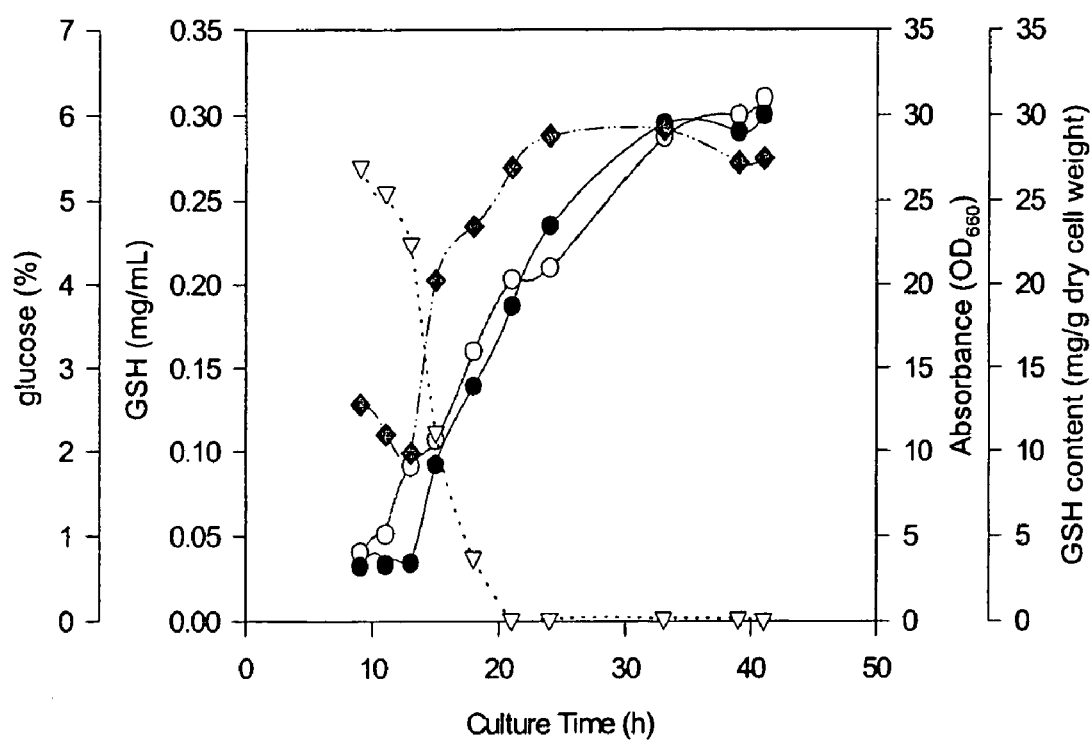
FIG. 6 Results of glutathione batch fermentation in a 5 L fermentor. (○): $OD_{660}$. (●): glutathione concentration (mg/ml). (♦): intracellular glutathione content (mg/g dry cell weight). (∇): glucose concentration (%).

YA03083 was utilized in the example. The results of the batch cultivation are shown in FIG. 6. After the batch cultivation for 40 hours, both the glutathione production per dry cell weight and the glutathione concentration per cell solution volume attained a stationary phase. The dry cell weight per liter was about 15 g; the glutathione concentration was 0.3 g/L; the glutathione weight per dry cell weight was 30 mg/g dry cell weight; on the other hand, the γ-glutamylcysteine production was a little raised.

Figure 7:
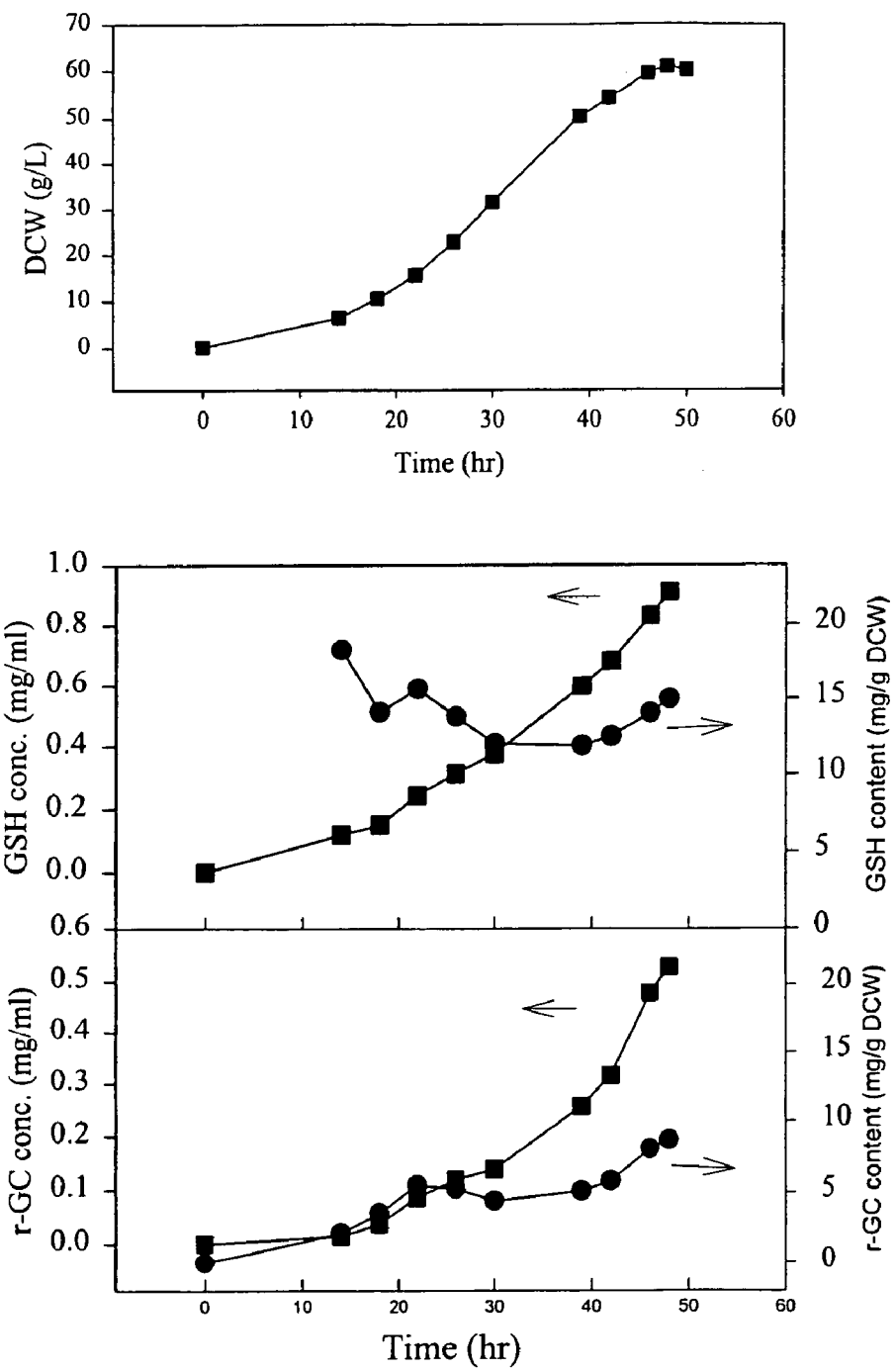
FIG. 7 Results of glutathione fed-batch fermentation in a 5 L fermentor. (●): glutathione concentration (mg/ml). (■): intracellular glutathione content (mg/g dry cell weight).

The results of the fed-batch cultivation are shown in FIG. 7. Cysteine and glycine were added to the culture medium. The cell density reached 60 g/L, which was much higher than 15 g/L measured in the batch fermentation, and 25 g/L reported (U.S. Pat. No. 4,582,801). Although the glutathione weight per dry cell weight of 15 mg/g dry cell weight was lower than 30 mg/g dry cell weight in the batch fermentation, the total glutathione concentration reached 1.0 mg/mL, which was much higher than 0.3 g/L in the batch fermentation.

In another aspect, γ-glutamylcysteine was also produced in the fed-batch cultivation. The content in the cells was 10 mg/g dry cell weight, and that in the medium was 0.5 mg/g dry cell weight. The productions of glutathione and γ-glutamylcysteine were both improved. It confirmed that continuously adding the amino acids improves glutathione and γ-glutamylcysteine productions and yeast cell density.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

What is claimed is:

1. A biologically pure culture of a microorganism strain comprising all characteristics of the *Saccharomyces cerevisiae* strain selected from the group consisting of YA02032 and YA03083, which culture has a characteristic nature capable of producing glutathione and the precursor thereof, γ-glutamylcysteine; wherein YA02032 is deposited at the Deutsche Sammlung von Mikroorganismen und Zellkulturen GmbH (DSMZ), Mascheroder Weg 1b, D38124, Braunschweig, Germany under accession number DSM 17789, and YA03083 is deposited at the Deutsche Sammlung von Mikroorganismen und Zellkulturen GmbH (DSMZ), MascheroderWeg 1b, D38124, Braunschweig, Germany under accession number DSM 17790.

2. The culture according to claim 1, wherein the strain is YA03083.

3. The culture according to claim 1, wherein the strain is YA02032.

4. A composition comprising the culture according to claim 1.

5. The composition according to claim 4, which is a pharmaceutical composition or a food composition.

6. A process for the production of glutathione and/or the precursor thereof, γ-glutamylcysteifle, which is characterized by cultivating the biologically pure culture of a microorganism strain according to claim 1.

7. The process according to claim 6, wherein the microorganism is *Saccharomyces cerevisiae* YA03083.

8. The process according to claim 6, wherein the microroganism is *Saccharomyces cerevisiae* YA02032.

9. The process according to claim 6, wherein the culture medium comprises at least one amino acid.

10. The process according to claim 9, wherein the at least one amino acid is selected from the group consisting of cysteine, glycine and glutamic acid.

11. The process according to claim 10, wherein the amino acid is cysteine.

12. The process according to claim 9, wherein the amino acid has a concentration in a range of 0.1% to 0.75%.

13. The process according to claim 9, wherein the amino acid is added to the culture medium at 15 to 48 hours from the beginning of fermentation.

14. The process according to claim 6, wherein the cultivation is a batch cultivation or fed-batch cultivation.

15. The process according to claim 14, wherein the cultivation is a fed-batch cultivation.

16. The process according to claim 6, wherein the microorganism is cultivated at a temperature in a range of 20 to 40° C.

17. The process according to claim 6, wherein the microorganism is cultivated at a pH value in a range of 3 to 7.

18. The process according to claim 6, wherein the microorganism is cultivated under an aerobic condition.

19. The process according to claim 6, further comprising the step of recovering glutathione and/or γ-glutamylcysteine from the culture medium.

20. A process for the production of glutathione and/or a precursor thereof γ-glutamylcysteine comprising cultivating the biologically pure culture of the microorganism strain according to claim 1; wherein the culture medium comprises at least one amino acid; and the at least one amino acid being added to the culture medium at 15 to 48 hours from the beginning of fermentation.

21. The process according to claim 20, wherein the at least one amino acid is selected from the group consisting of cysteine, glycine and glutamic acid.

22. The process according to claim 20, wherein the at least one amino acid has a concentration in a range of 0.1% to 0.75%.

23. The process according to claim 20, wherein the cultivation is a batch cultivation or fed-batch cultivation.

24. The process according to claim 23, wherein the cultivation is a fed-batch cultivation.

25. The process according to claim 20, wherein the microorganism is cultivated at a temperature in a range of 20 to 40° C.

26. The process according to claim 20, wherein the microorganism is cultivated at a pH value in a range of 3 to 7.

27. The process according to claim 20, wherein the microorganism is cultivated under an aerobic condition.

28. The process according to claim 20, further comprising the step of recovering glutathione and/or γ-glutamylcysteine from the culture medium.

29. A process for producing a strain of *Saccharomyces cerevisiae* that overproduces glutathione comprising the steps of:
   (a) providing a wild-type strain of *Saccharomyces cerevisiae*;
   (b) subjecting the wild-type strain to mutagenesis with N-methyl-N'-nitro-N-nitrosoguanidine (NTG) to obtain NTG-treated strains;
   (c) subjecting the NTG-treated strains to a screening medium comprising an oxidant or toxin or both selected from the group consisting of 1,2,4-triazole, sodium azide, benzyl chloride and methylglyoxal; and
   (d) screening for a mutant strain that produces glutathione in an amount of greater than 5 to 8 mg/g of dry cells wherein said mutant is selected from the group consisting of YA02032 (DSM 17789) and YA03083 (DSM 17790).

* * * * *